(12) United States Patent
Van Antwerp et al.

(10) Patent No.: US 6,852,694 B2
(45) Date of Patent: Feb. 8, 2005

(54) STABILIZED INSULIN FORMULATIONS

(75) Inventors: William Peter Van Antwerp, Valencia, CA (US); Poonam S. Gulati, La Canada, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 10/080,034

(22) Filed: Feb. 21, 2002

(65) Prior Publication Data

US 2002/0132760 A1 Sep. 19, 2002

Related U.S. Application Data

(60) Provisional application No. 60/270,374, filed on Feb. 21, 2001.

(51) Int. Cl.[7] .............................................. A61K 38/00
(52) U.S. Cl. .......................... 514/13; 514/13; 514/33; 514/12; 514/4; 530/303; 530/304; 530/325
(58) Field of Search ................................ 514/13, 3, 12, 514/4; 530/303, 304, 325, 333, 338

(56) References Cited

U.S. PATENT DOCUMENTS

| | | |
|---|---|---|
| 4,431,740 A | 2/1984 | Bell et al. |
| 4,608,364 A | 8/1986 | Grau |
| 4,652,525 A | 3/1987 | Rutter et al. |
| 4,652,548 A | 3/1987 | Chance et al. |
| 4,701,440 A | 10/1987 | Grau |
| 4,783,441 A | 11/1988 | Thurow |
| 4,801,684 A | 1/1989 | Grau |
| 4,885,164 A | 12/1989 | Thurow |
| 4,988,675 A | 1/1991 | Froesch et al. |
| 5,149,777 A * | 9/1992 | Hansen et al. |
| 5,514,646 A | 5/1996 | Chance et al. |
| 5,527,307 A | 6/1996 | Srisathapat et al. |
| 5,569,186 A | 10/1996 | Lord et al. |
| 5,637,095 A | 6/1997 | Nason et al. |
| 5,641,744 A | 6/1997 | Cooper |
| 5,753,681 A | 5/1998 | Fujiwara et al. |
| 5,783,556 A | 7/1998 | Clark et al. |
| 5,958,909 A | 9/1999 | Habener |
| 6,034,054 A | 3/2000 | DeFilippis et al. |
| 6,136,784 A | 10/2000 | L'Italien et al. |
| 6,153,632 A | 11/2000 | Rieveley |
| 6,166,042 A | 12/2000 | Ikeda et al. |
| 6,166,043 A | 12/2000 | Ikeda et al. |
| 6,169,099 B1 | 1/2001 | Ikeda et al. |
| 6,169,100 B1 | 1/2001 | Ikeda et al. |
| 6,268,343 B1 | 7/2001 | Knudsen et al. |
| 6,514,937 B1 * | 2/2003 | Mascarenhas |

FOREIGN PATENT DOCUMENTS

| | | |
|---|---|---|
| EP | 0 837 072 A2 * | 4/1998 |
| WO | WO 92/20366 | 11/1992 |
| WO | WO 96/02270 A1 | 2/1996 |
| WO | WO 96/10417 A1 | 4/1996 |
| WO | WO 97/12988 | 4/1997 |
| WO | WO 98/57636 | 12/1998 |
| WO | WO 99/43705 | 9/1999 |
| WO | WO 99/64598 A2 | 12/1999 |
| WO | WO 01/00223 A2 | 1/2001 |

OTHER PUBLICATIONS

Ahren et al., "Effects of Glucagon–Like Peptide–1 on Islet Function and Insulin Sensitivity in Noninsulin–Dependent Diabetes Mellitus," Jnl. Clin. Endocrinology and Metabolism, 1997, 82(2): 473–478.

Brange et al., "Chemical Stability of Insulin," Acta. Pharm. Nord., 1992, 4(4): 223–232.

Gutniak et al., "Antidiabetogenic Effect of Glucagon–Like Peptide–1 (7–36) Amide in Normal Subjects and Patients with Diabetes Mellitus," The New England Jnl. Of Med., 1992, 326(20): 1316–1322.

Holst, "GLP–1 in NIDDM," Diabet. Med., 1996, vol. 9 (supp. 6): S156–160.

Mokuda et al., "Plasma Glucose Response After Intravenous Injection of Tolbutamide in Insulin–Treated Type I and Type II Diabetic Patients," Exp. Clin. Endocrinol., 1988, 91(3): 265–270.

Ryan et al., "Insulinotropic Hormone Glucagon–Like Peptide–1–(7–37) Appears Not to Augment Insulin–Mediated Glucose Uptake in Young Men During Euglycemia," Jnl. Clin. Endocrinology and Metabolism, 1998, 83(7): 2399–2404.

Toft–Nielson et al., "The Effect of Glucagon–Like Peptide I (GLP–I) on Glucose Elimination in Healthy Subjects Depends . . . Hormones," Diabetes, 1996, 45(5): 552–556.

* cited by examiner

Primary Examiner—Christopher R. Tate
Assistant Examiner—B. Dell Chism
(74) Attorney, Agent, or Firm—Gates & Cooper LLP

(57) ABSTRACT

The present invention is directed to stabilized insulin composition comprising a mixture of insulin species such as insulin and an insulin analog. As disclosed herein, insulin compositions comprising a mixture of insulin and insulin analog species form heterodimeric complexes having a greater stability than the homodimeric complexes formed in compositions comprising single insulin species. Consequently, the present invention provides methods for stabilizing insulin molecules, methods for identifying stable heterodimeric insulin complexes and stabilized insulin compositions.

14 Claims, 3 Drawing Sheets ically agitated inside a metal container (typically titanium) having a relatively hydrophobic surface (e.g. $TiO_2$ with an average contact angle of more than 60°).
STABILIZED INSULIN FORMULATIONS

RELATED APPLICATIONS

This application claims priority under Section 119(e) from U.S. Provisional Application Ser. No. 60/270,374, filed Feb. 21, 2001; and this application is related to U.S. application Ser. No. 09/344,676, filed Jun. 25, 1999, the contents of each of which are incorporated herein by reference.

BACKGROUND OF THE INVENTION

1. Field of the Invention.

The present invention relates to compositions and methods for use in the treatment of pathologies associated with insulin deficiency.

2. Description of Related Art.

In continuous infusion systems, a fluid containing a therapeutic agent is pumped from a reservoir, usually to a subcutaneous, intravenous, or intraperitoneal depot. The reservoir, which is refilled periodically, is attached to the patient's body, or is implanted in the patient's body. In either case, the patient's body heat and body motion, plus turbulence in the tubing and pump impart a relatively high amount of thermo-mechanical energy to the formulation. In the interest of minimizing the frequency with which the reservoir is refilled, and of minimizing the size of the reservoir, stable formulations having a relatively high concentration of the therapeutic agent are highly advantageous. Consequently, stable formulations of therapeutic agents are particularly important for use in delivery devices that expose these agents to elevated temperatures and/or mechanical stress.

A typical context for such continuous infusion systems involves the treatment of diabetes and related syndromes by the administration of insulin and its analogs. Stable insulin formulations, for example, are required for use in continuous infusion systems and related devices. Insulin formulations for implantable pump use preferably possess several characteristics including exceptional physical and chemical stability. Commercial insulin preparations are typically designed to have a stable shelf life of 1 to 2 years when stored at refrigerator temperatures in glass vials or cartridges. In actual use however, insulin is typically used in a syringe (for immediate injection) in an insulin pump (for up to a week) or in an insulin pen (for a week or two). Formulations of insulin for use in continuous infusion systems should remain soluble and substantially free of aggregation, even though subjected to the patient's body heat and motion for periods ranging from a few days to several months. In this context, instability is promoted by the higher insulin concentrations that are desirable for continuous infusion systems and by the thermo-mechanical stress to which formulations are exposed in continuous infusion systems. Therefore, improvement in the physical and chemical stability of concentrated insulin formulations is urgently needed to facilitate their use in continuous infusion systems. In particular, the preferred insulin formulations for implantable pump use possess chemical and physical stability in the harsh environment of the implantable pump. The formulations are typically stable in a glass cartridge or vial during long term storage and in addition should be stable for at least 90 days at physiological temperatures, all while being constantly agitated inside a metal container (typically titanium) having a relatively hydrophobic surface (e.g. $TiO_2$ with an average contact angle of more than 60°).

The development of insulin analogs for the treatment of diabetes allows for the generation of novel formulations for use in continuous infusion devices. For example, rapid-acting insulins, known as monomeric insulin analogs, are well-known in the art, and are disclosed in Chance, et al. U.S. Pat. No. 5,514,646, issued May 7, 1996; Brems, et al., Protein Engineering, 6:527–533 (1992); Brange, et al., EPO publication No. 214,826 (published Mar. 18, 1987); and Brange, et al., Current Opinion in Structural Biology 1:934–940 (1991). Monomeric insulin analogs are absorbed much faster than insulin, and are ideally suited for postprandial control of blood glucose levels in patients in need thereof. They are also especially well-suited for administration by continuous infusion for both prandial and basal control of blood glucose levels because of their rapid absorption from the site of administration. Unfortunately, monomeric insulin analog formulations have a propensity to aggregate and to become unstable when exposed to thermo-mechanical stress. Aggregation may even be manifested as precipitation of higher-order insulin species. In this way, aggregation can prevent reproducible delivery of effective therapeutic doses of monomeric insulin analogs, and may also cause irritation at the administration site or a more systemic immunological response. Consequently, insulin analog formulations stabilized against aggregation are highly desirable.

While a number of aqueous formulations which stabilize insulin compositions have been identified in the art, the destabilization of insulin in solution continues to create problems for medical practitioners. Consequently, there is a need for new insulin compositions which overcome the problems of the prior art. This need is fulfilled by the invention that is described below.

SUMMARY OF THE INVENTION

The present invention provides methods of stabilizing insulin molecules in solution as well as stabilized insulin compositions. A preferred embodiment of the invention is a composition which includes a combination of a first insulin species and a second insulin species, where the first and second insulin species are selected to generate a composition that is more stable than a composition having only the first insulin species or a composition having only the second insulin species. A related embodiment of the invention is a composition which includes a first insulin species and a second insulin species, wherein the first insulin species and the second insulin species form a heterodimeric complex; and wherein the first insulin species and the second insulin species are selected so that the heterodimeric complex is more stable than a homodimeric complex formed by the first insulin species or a homodimeric complex formed by the second insulin species.

Yet another embodiment of the invention is a method of making an insulin composition by combining a first insulin species and a second insulin species under conditions that allow the formation of a heterodimeric complex and where the first insulin species and the second insulin species are selected to form a heterodimeric complex that is more stable than a homodimeric complex formed by the first insulin species or a homodimeric complex formed by the second insulin species. A related embodiment of the invention is a method of making an insulin composition by combining a first insulin species and a second insulin species where the resulting composition is more stable than a composition having only the first insulin species or a composition having only the second insulin species. Yet another embodiment of the invention is a method of stabilizing an insulin composition that consists of a first insulin species and a second insulin species by specifically selecting the first and second insulin species in order to generate a composition that is more stable than a composition having only the first insulin species or a composition having only the second insulin species. Another embodiment of the invention consists of a method of stabilizing an insulin polypeptide prone to aggregation by combining the insulin polypeptide with an insulin analog polypeptide in an amount sufficient to form an insulin polypeptide/insulin analog polypeptide heterodimer, wherein the insulin polypeptide/insulin analog polypeptide heterodimer is more stable than either an insulin polypeptide/insulin polypeptide homodimer or an insulin analog polypeptide/insulin analog polypeptide homodimer.

Another embodiment of the invention is a method for identifying a stabilized insulin composition which includes the steps of combining a first insulin species with a second insulin species so that a heterodimeric complex formed from the first and second insulin species is generated, comparing the stability of the heterodimeric complex formed from the first and second insulin species with the stability of a homodimeric complex formed from the first insulin species or a homodimeric complex formed from the second insulin species and identifying a formulation wherein the heterodimeric complex formed from the first and second insulin species is more stable than homodimeric complex formed from the first insulin species or a homodimeric complex formed from the second insulin species. A related embodiment of the invention is a method for identifying a stabilized insulin composition which includes the steps of combining a first insulin species with a second insulin species and comparing the stability of the formulation having a combination of the first and second insulin species with the stability of a formulation having only the first insulin species or a formulation having only the second insulin species and identifying an insulin composition wherein the formulation generated by combining the first and second insulin species is more stable than a formulation having only the first insulin species or a formulation having only the second insulin species.

As disclosed herein, the relative stability of compositions having the first and second insulin species can be determined by a number of methods known in the art. Preferably the stability of the compositions are determined by a spectrophotometric assay of turbidity or an assay with Thioflavin-T (as illustrated, for example in Example 2).

Typical embodiments of the invention are compositions and methods where the first insulin species is human insulin and the second insulin species is a variant of human insulin having at least one amino acid substitution such as LISPRO insulin. In such embodiments, the human insulin preferably comprises from about 1% to about 50% of the insulin of the composition (and more preferably from about 5% to about 20%) and wherein the LISPRO insulin comprises from about 50% to about 99% of the insulin of the composition (from about 95% to about 80%). As is known in the art, these the compositions can include a variety of factors such as pharmaceutical carriers.

Related embodiments of the invention include the use of the methods and compositions disclosed herein in the treatment of pathologies associated with insulin deficiency. Preferably the compositions disclosed herein are used in a mechanical infusion device such as a continuous infusion pump.

DETAILED DESCRIPTION OF THE INVENTION

Definitions

Figure 1:
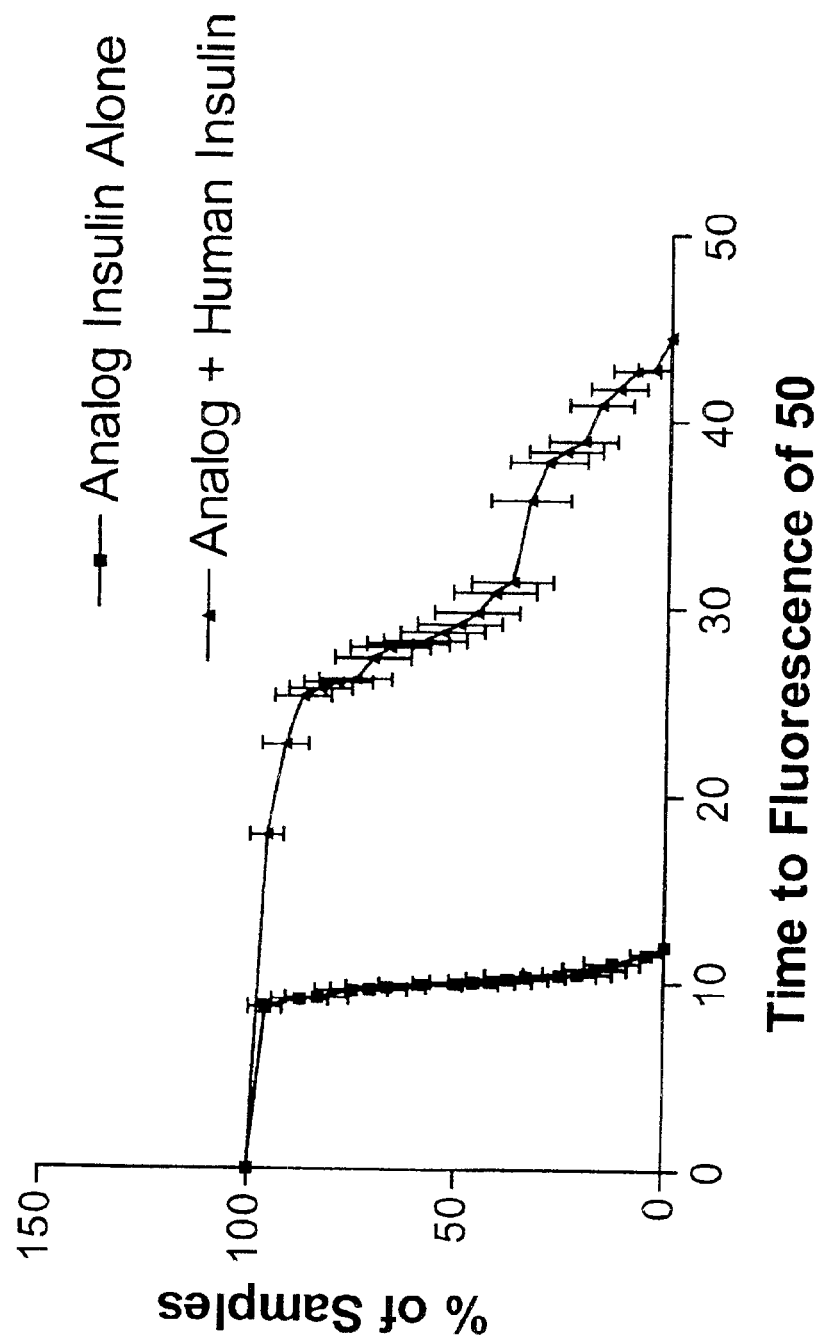
FIG. 1 shows a Thioflavin-T analysis of a U 100 formulation of LISPRO analog insulin alone as well as a combination of LISPRO analog insulin and human insulin (10% U). The figure provides a representative Kaplan-Meier survival curve analysis of the increase in sample fluorescence of these formulations over time. The survival curves provide a comparison between a formulation of the analog alone as compared to a formulation of the analog combined with human insulin.
Figure 2:
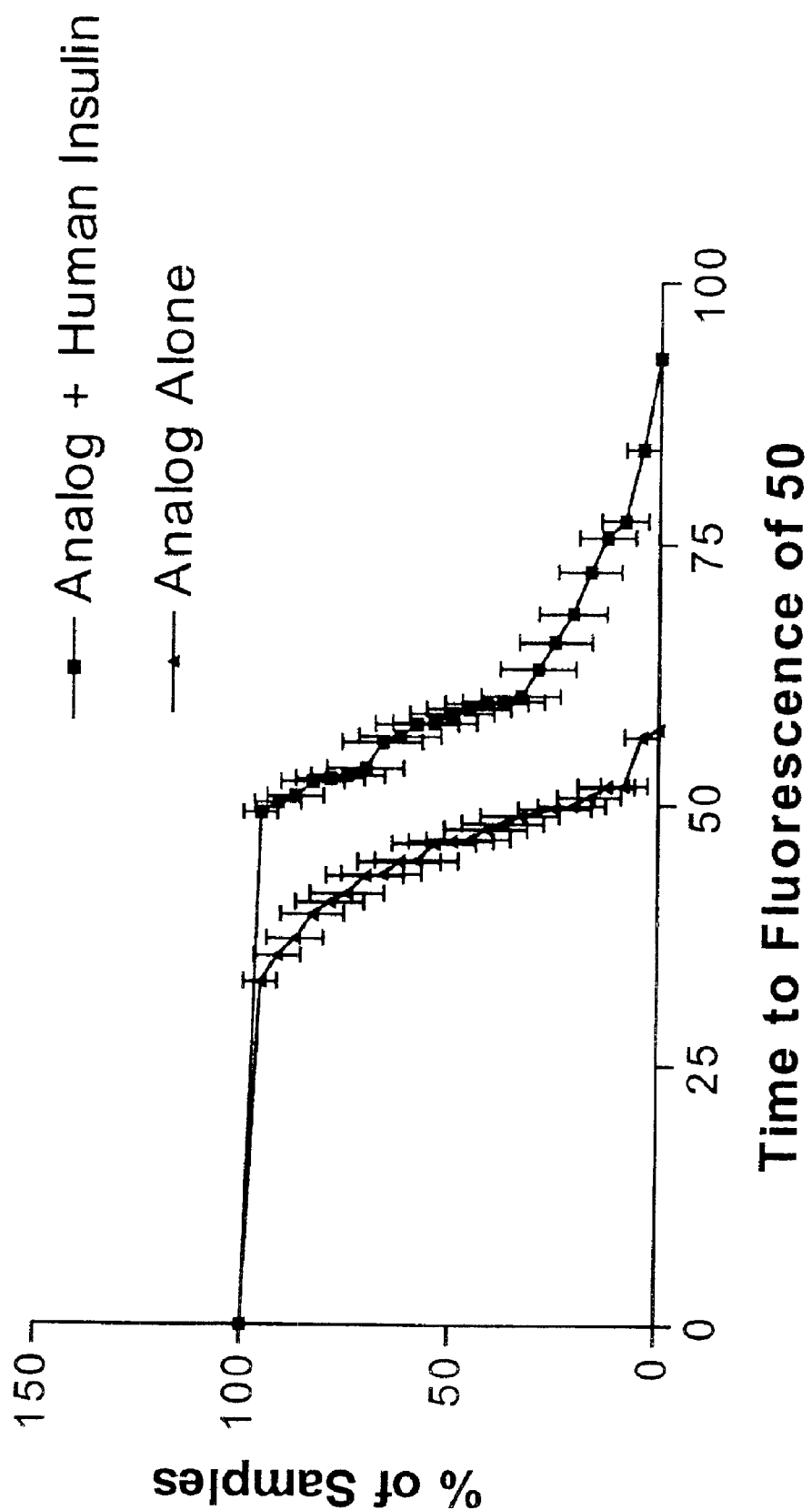
FIG. 2 shows a Thioflavin-T analysis of a U 400 formulation of LISPRO analog insulin alone as well as a combination of LISPRO analog insulin and human insulin (10% U). The figure provides a representative Kaplan-Meier survival curve analysis of the increase in sample fluorescence of these formulations over time. The survival curves provide a comparison between a formulation of the analog alone as compared to a formulation of the analog combined with human insulin.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted. For purposes of the present invention, as disclosed and claimed herein, the following terms and abbreviations have the following meanings.

As used herein, the terms "stable" "stabilized" and "stability" are used according to their broadest meaning and refer to the physical and chemical and/or biological stability of formulations of polypeptides such as insulin species. Instability in a protein formulation typically results in a decrease in the biological activity of the formulation over time. Loss of biological activity may be caused, for example, by the aggregation of the protein molecules which can form higher order polymers or even precipitates. For example, insulin has a propensity to aggregate when exposed to thermo-mechanical stress. A "stable" or "stabilized" formulation is one wherein a loss of biological activity associated with the instability of a formulation is reduced. As is known in the art, the relative stability of a formulation can be assessed, for example, by comparative analyses of the properties of a control formulation (e.g. one consisting exclusively of insulin homodimers and related complexes) with a formulation under investigation (e.g. one including insulin heterodimer and related complexes). A "stable" or "stabilized" protein complex such as a stable heterodimeric complex is one in which the species that make up the complex and/or factors controlling the interaction of these species (e.g. the individual properties of the members of the complex, the kinetics of their association, their affinity for each other etc.) are modulated in a way that optimizes the biological activity of the composition. Stability, such as physical stability may be assessed by methods well-known in the art, including measurement of a sample's apparent attenuation of light (absorbance, or optical density). Such a measurement of light attenuation relates to the turbidity of a formulation. Turbidity is produced by aggregation or precipitation of proteins or complexes in the formulation. Other methods for assessing physical stability are well-known in the art.

The various forms of the verb "to aggregate" refer to a process whereby individual molecules or complexes associate to form aggregates. An exemplary aggregate is a polymeric assembly having molecules or complexes of monomeric insulin analog. Monomeric insulin analogs, and hexamer complexes thereof, have a propensity to aggregate when, for example, they are exposed to thermo-mechanical stress. Aggregation can proceed to the extent that a visible precipitate is formed.

The term "complex" means a composition having two or more parts, such as a compound in which a transition metal is coordinated to at least one ligand. Ligands include nitrogen-containing molecules, such as proteins, peptides, amino acids, and TRIS, among many other compounds. Monomeric insulin analog can be a ligand of divalent zinc ions.

The term "analog" refers to a molecule that is structurally similar or shares similar or corresponding attributes with another molecule (e.g. an insulin variant capable of forming an insulin/insulin dimer complex). The term "homolog" refers to a molecule which exhibits homology to another molecule, by for example, having sequences of chemical residues that are the same or similar at corresponding positions. For example, insulin LISPRO is an analog of human insulin where the B28 Proline and B29 Lysine are interchanged. The effects of this change are to fundamentally decrease the propensity to form the hexameric insulin structure and to increase the relative amount of insulin monomer present in solution. DeFelippis and colleagues in U.S. Pat. No. 6,034,054 describe a formulation of LISPRO insulin analog that shows remarkable physical stability when measured in-vitro. The term "variant" refers to a molecule that exhibits a variation from a described type or norm, such as a protein that has one or more different amino acid residues in the corresponding position(s) of a specifically described protein (e.g. LISPRO insulin is a variant of human insulin). Those skilled in the art understand that the terms analog, homolog and variant are not mutually exclusive and that various molecules can meet more than one of these definitions.

The term "species" such as in "insulin species" is used according to its art accepted meaning and refers to those mammalian insulin proteins having a biological activity that allows them to be used in the treatment of diabetes such as human insulin and insulins from non-human mammals as well as variants of human insulin (e.g. porcine insulin and LISPRO insulin). Non-human insulin species generally share at least about 90% or more amino acid homology with human insulin (e.g. using BLAST criteria). The structure of human insulin is disclosed in Nature 187,483 (1960). A review of the research, development, and recombinant production of human insulin is found in Science 219, 632–637 (1983). See also U.S. Pat. Nos. 4,652,525 (rat insulin) and 4,431,740 (human insulin).

The terms "monomeric human insulin analog", "monomeric insulin analog" and "human insulin analog" are well-known in the art, and refer generally to fast acting analogs of insulin (typically human insulin), which include: human insulin, wherein Pro at position B28 is substituted with Asp, Lys, Leu, Val, or Ala, and wherein position B29 is Lys or is substituted with Pro; AlaB26-human insulin, des(B28–B30) human insulin; and des(B27) human insulin. Such monomeric insulin analogs are disclosed in U.S. Pat. No. 5,514,646, WO 99/64598, WO 99/6459A2 and WO 96/10417A1.

The term "TRIS" refers to 2-amino-2-hydroxymethyl-1,3,-propanediol, and to any pharmacologically acceptable salt thereof. The free base and the hydrochloride form are two common forms of TRIS. TRIS is also known in the art as trimethylol aminomethane, tromethamine, and tris (hydroxynethyl)aminomethane.

The term "arginine" refers to the amino acid and encompasses the D- and L-enantiomers as well as mixtures thereof The term also includes any pharmacologically acceptable salts thereof. Arginine is also known in the art as 1-amino-4-guanidinovaleric acid.

The term "phenolic preservative" as used herein, typically refers to art accepted phenolic preservatives such as chlorocresol, m-cresol, phenol, or mixtures thereof.

An "isotonicity agent" is a compound that is physiologically tolerated and imparts a suitable tonicity to a formulation to prevent the net flow of water across cell membranes that are in contact with the formulation. Compounds, such as glycerin, are commonly used for such purposes at known concentrations. Other possible isotonicity agents include salts, e.g., sodium chloride, dextrose, and lactose.

The term "administer" means to introduce formulation of the present invention into the body of a patient in need thereof to treat a disease or condition.

The term "continuous infusion system" refers to a device for continuously administering a fluid to a patient parenterally for an extended period of time or for, intermittently administering a fluid to a patient parenterally over an extended period of time without having to establish a new site of administration each time the fluid is administered. The fluid contains a therapeutic agent or agents. The device has a reservoir for storing the fluid before it is infused, a pump, a catheter, or other tubing for connecting the reservoir to the administration site via the pump, and control elements to regulate the pump. The device may be constructed for implantation, usually subcutaneously. In such a case, the insulin reservoir will usually be adapted for percutaneous refilling. Obviously, when the device is implanted, the contents of the reservoir will be at body temperature, and subject to the patient's body motion.

The term "treating" refers to the management and care of a patient having a pathology such as diabetes or hyperglycemia, or other condition for which insulin (or other polypeptide) administration is indicated for the purpose of combating or alleviating symptoms and complications of those conditions. Treating includes administering a formulation of present invention to prevent the onset of the symptoms or complications, alleviating the symptoms or complications, or eliminating the disease, condition, or disorder.

Characterization of the Invention

Embodiments of the present invention provide improved methods and materials for maintaining the stability of insulin formulations by inhibiting the destabilization of the biologically active insulin polypeptides therein. While preferred embodiments of the invention apply to insulin formulations that can be used in different contexts, it is particularly useful in continuous infusion systems where a device continuously administers a fluid to a patient parenterally for an extended period of time or for, intermittently administering a fluid to a patient parenterally over an extended period of time without having to establish a new site of administration each time the fluid is administered.

Typical regular insulin formulations include insulin in an un-buffered or phosphate buffered solution containing glycerin for isotonicity, zinc ions for stability and a phenolic preservative such as phenol or m-cresol. These formulations are generally not sufficiently stable, either chemically or physically, for use in implantable pumps with the exception being insulin in a formulation of Tris (tris-hydroxymethyl amino methane) buffer and Genapol, a polyoxyethylene, polyoxypropylene copolymer non-ionic surfactant (see e.g. U.S. Pat. No. 4,783,441). In addition to using regular insulin in such formulations, insulin analogs such as LISPRO can also be used (see e.g. U.S. Pat. No. 6,034,054). Unfortunately, the very physically stable LISPRO formulations are unacceptable for certain in-vitro uses such as in infusion pumps.

In a series of parallel experiments using a diabetic canine model, implantable pumps were used with either LISPRO or regular insulin-Genapol formulations. Interestingly, the addition of Genapol to insulin analog LISPRO formulations greatly decreases the in-vitro physical stability of these polypeptides, suggesting that there is a different mechanism for aggregation in LISPRO formulations than in regular insulin formulations. While the regular insulin-Genapol formulations showed the expected 90-day stability, catheter blockages were observed with the LISPRO formulations after only a few weeks. The catheters exposed to the LISPRO formulations were blocked with material that was identified by mass spectroscopy as a mixture of insulin and Tris in a 10/90 ratio. This surprising finding suggests a potential mechanism of LISPRO precipitation followed by LISPRO-Tris interaction coupled with reaction of $CO_2$ with the Tris to form the di-Tris carbamide.

The advantages of various embodiments of the invention are clarified when one considers problems associated with the instability of insulin formulations. The chemical stability of insulin is primarily governed by two main reactions, both of which are temperature dependent. A first destabilizing reaction that occurs in more acidic conditions is the deamidation of the $A^{21}$ and $B^3$ positions. A second set of destabilizing reactions occur at relatively higher pH values and involve changes in the disulfide linkages that define the structure of the insulin molecule. Insulin and its analogs contain three disulfide bonds, two between the A and B chains and one that joins two portions of the A chain. At relatively higher pH values these disulfide linkages can be broken and occasionally scrambled. The molecules that result from disulfide breaking have no biological activity and can lead to further aggregation of insulin in an autocatalytic reaction. The physical stability of insulin is primarily governed by two major factors, the presence of any insulin molecules that have had disulfide linkages disrupted or by insulin monomers that have been denatured by contact with hydrophobic surfaces. Physical instability is manifested as aggregation of the insulin (turbidity) and the generation of high molecular weight insulin polymers. Neither the aggregates nor the polymers have insulin biological activity and insulin aggregates have been suggested as potential causes of elevated levels of anti-insulin antibodies.

Figure 3:
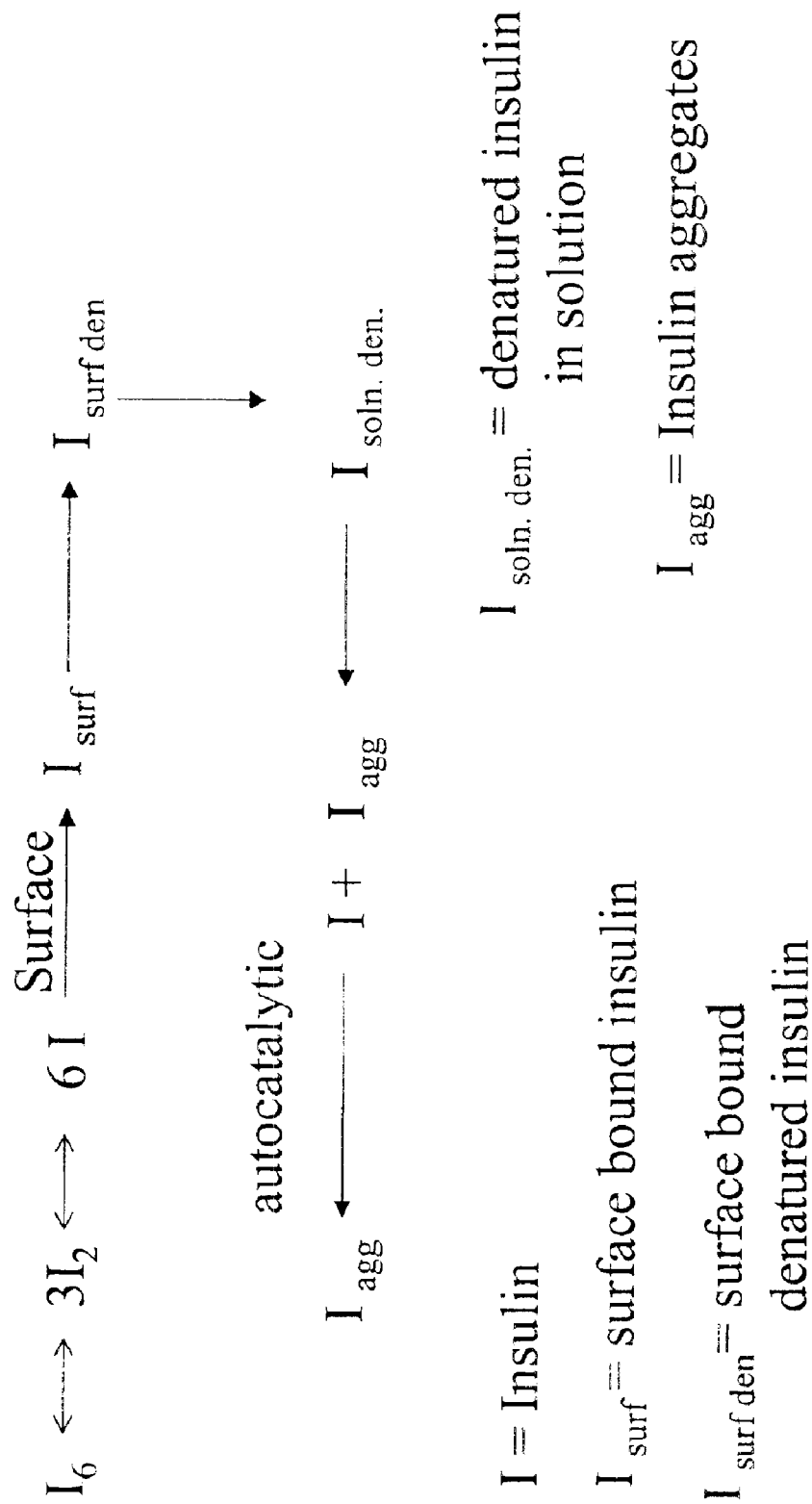
FIG. 3 provides a schematic of a mechanism of insulin aggregation.

Insulin chemical stability is predominately thermally driven, with no large differences between chemical stability in the pump and in the glass primary packaging. Physical stability however is strongly dependent on both the formulation and the materials and shapes of the materials that are in contact with the insulin. In 1997, a model of insulin/pump interactions was published that showed the importance of an interaction between the free insulin monomer in the formulation with the surface of the pump (Proceedings of AIDSPIT (Artificial Insulin Delivery Systems, Pancreas and Islet Transplant) meeting, February, 1997). The model is captured in the equation shown in FIG. 3 which is summarized below:

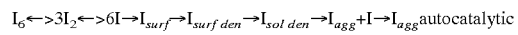

$I_6 \leftarrow\rightarrow 3I_2 \leftarrow\rightarrow 6I \rightarrow I_{surf} \rightarrow I_{surf\,den} \rightarrow I_{sol\,den} \rightarrow I_{agg} + I \rightarrow I_{agg}$ autocatalytic This equation says that insulin in solution in a container such as a bottle or pump is an equilibrium between the insulin hexamer, dimer and monomer. Insulin monomer can deposit on a surface to make $I_{surf}$. On the surface, insulin can denature to make $I_{surf\,den}$. Denatured insulin can then fall off the surface to make $I_{sol\,den}$, denatured insulin in solution. This insulin is the seed for aggregation and once aggregates form, even soluble aggregates; they react in an autocatalytic manner with insulin monomer to form further aggregates. This model provides insight into methods of stabilizing insulin that allow the skilled artisan to make a variety of stabilized insulin formulations. For example, by reducing the amount of monomeric insulin in an insulin composition, the overall aggregation and destabilization of the insulin molecules in the solution is reduced.

Without being bound by a specific theory, by using data pertaining to insulin instability, embodiments of the invention disclosed herein address the above noted problems by identifying formulation conditions which enhance insulin stability thereby facilitating its use, particularly in pump infusion systems. Specifically, the observation that insulin analog formulations contain significantly more monomer than regular human insulin formulations coupled with knowledge that insulin monomer can denature on the surface of the infusion set tubing, provides evidence that formulations which decrease the relative amount of insulin monomer that can denature on a surface provide for more stable compositions. In this context circular dichroism (CD) analysis data presented herein demonstrates that the insulin molecules in a heterodimer consisting of insulin and an insulin analog (e.g. insulin/LISPRO) are mote strongly bound (e.g. are mote stable) than insulin molecules in a LISPRO/LISPRO homodimer (see e.g. Example 1 below). Moreover, as illustrated in the Examples below, formulations consisting of a mixture of insulin and insulin analog (e.g. LISPRO) are more stable than formulations having only insulin analog alone. Without being bound by a specific theory, data provides evidence that the stability of this heterodimer decreases the relative amount of insulin monomer that is present in solution (and prone to denaturation on a surface such as the surface of an infusion pump). Consequently, the inclusion of an amount of regular human insulin (typically a few percent) in an analog formulation can ameliorate instability by essentially scavenging and stabilizing any analog monomer that exists in the formulation.

A mixture of regular human insulin with an insulin analog prone to aggregation (typically the LISPRO insulin analog) generates insulin formulations having enhanced stability. Typical formulations of the invention use a small amount of regular human insulin to stabilize the analog formulation. While any amount of regular insulin sufficient to allow the formation of a stabilizing heterodimer will generate the stabilized formulations of the invention, typically the mixture comprises between about 1% to about 50% human insulin and about 50% to about 99% of an insulin analog prone to aggregation (typically LISPRO). These mixtures preserve the benefits of the analog such as improved physical stability against aggregation and physical insult and increased bioavailability as compared to regular insulin while maintaining the chemical stability of the parent formulations and the benefits of the improved bioavailability and improved pharmacokinetics of the insulin analogs. Without being bound by a specific theory or model, the data provided herein provides evidence that the stabilizing mechanism involves the formation of a stable insulin/insulin-analog heterodimer that has in effect scavenged the analog monomer before it can denature on the surface of the device or the tubing. Such a mechanism would contribute to the stability of an insulin formulation by reducing the effective concentration of insulin monomer present in a solution that can lose its activity in this manner. Such formulations have been shown to work effectively in-vivo and are suitable for use in man. Consequently, the novel insulin analog/insulin formulation disclosed herein will improve the stability of insulin in a variety of contexts including implantable and external insulin pump therapy.

The formulation disclosure provided herein enhances the therapeutic delivery of biologically active insulin in a number of contexts. For example, it is well known that some patients who use programmable external insulin pumps and insulin LISPRO (CSII, Continuous Subcutaneous Insulin Infusion) suffer from premature site loss. Thus site loss manifests itself by unexplained hyperglycemia in the absence of any discernable pump malfunction. Typically, patients using CSII will program a meal bolus appropriate for the meal and have an unexplained hyperglycemia several hours later. In most cases, the pump actually delivers the appropriate amount of insulin from the pump reservoir, but no concomitant blood glucose diminution occurs. There are several plausible explanations for these phenomena including a significant loss of insulin potency in the pump reservoir, anti-insulin antibodies, insulin degradation at the tip of the subcutaneous infusion set and others. The cause of site loss is likely to involve a biological response to infusion of denatured or partially denatured insulin monomer. Further, local cellular responses to unfolded proteins ate likely to evoke a localized production of non-specific protease activity. The use of a few percent of regular human insulin in an analog formulation will ameliorate the site loss by essentially scavenging (i.e. interacting with and stabilizing) any analog monomer that exists in the formulation.

The discovery that an insulin/insulin analog formulation provides enhances insulin stability is unexpected in view of art which directs artisans to utilize formulations which employ a single insulin species such as insulin or LISPRO.

The insulin formulations of the present invention are specifically designed to address problems in the art related to the destabilization of insulin species, a phenomena which can be measured by a number of procedures known in the art.

Formulations of the Invention

As described herein, the inclusion of an amount of regular human insulin (typically a few percent) in an analog formulation can ameliorate instability by essentially scavenging and stabilizing any analog monomer that exists in the formulation. Consequently, the formulations provided herein include an insulin analog combined with insulin in an amount sufficient to allow the generation of a stabilizing insulin/insulin analog heterodimer. The basis for the individual insulin and insulin analog components of the mixtures described herein can be found in art describing typical formulation having only insulin or only insulin analogs.

Typical regular insulin formulations include insulin in an un-buffered or phosphate buffered solution containing glycerin for isotonicity, zinc ions for stability and a phenolic preservative such as phenol or m-cresol. These formulations are not sufficiently stable, either chemically or physically, for use in implantable pumps. In the history of implantable pump therapy (1979 to present) there has been only one commercially acceptable formulation due to the original work of Thurow and Geissen and expanded by Grau (for typical related art, see e.g. U.S. Pat. Nos. 4,608,364, 4,701,440, 4,801,684, 4,783,441 and 4,885,164). This formulation is described in U.S. Pat. No. 4,783,441 to Thurow et al., assigned to Hoechst (now Aventis) and is similar to the regular insulin formulations with the exception that the buffer system is Tris (tris-hydroxymethyl amino methane) and with the addition of Genapol, a polyoxyethylene, polyoxypropylene copolymer non-ionic surfactant. It has been speculated that the Genapol surfactant either surrounds the insulin molecule in solution thus guaranteeing a hydrophilic environment for the insulin, or that the Genapol coats the surfaces of the device limiting the potential for insulin monomer to denature on the surface.

Typical insulin analog formulations include insulin analog in an unbuffered or phosphate buffered solution containing glycerin for isotonicity, zinc ions for stability and a phenolic preservative such as phenol or m-cresol. Insulin LISPRO is an analog of human insulin where the B28 Proline and B29 Lysine are interchanged. The effects of this change are to fundamentally decrease the propensity to form the hexameric insulin structure and to increase the relative amount of insulin monomer present in solution. DeFelippis and colleagues in U.S. Pat. No. 6,034,054 describe a formulation of LISPRO insulin analog that shows remarkable physical stability when measured in-vitro. This formulation is similar to the implantable insulin formulation described by Thurow et al. in U.S. Pat. No. 4,783,441, however the Tris concentration is three fold lower and there is no Genapol in the formulation. Interestingly, addition of Genapol to the insulin LISPRO formulation greatly decreases the in-vitro physical stability suggesting that there is a different mechanism for aggregation in LISPRO formulations than in regular insulin formulations. Moreover, LISPRO formulations are remarkably physically stable when tested in-vitro in a standard physical insult model compared to regular human insulin formulations and the LISPRO preparation shows almost identical chemical stability compared to regular insulin. In spite of these findings, the in-vivo and in-vitro stability of the LISPRO in a catheter occlusion model in the presence of $CO_2$ is markedly less than the regular human insulin formulations.

Unfortunately, the in-vivo data suggest that the very physically stable LISPRO formulations described by DeFilippis et al. in U.S. Pat. No. 6,034,054 are not acceptable in-vivo. Specifically, in a series of parallel experiments using a diabetic canine model, implantable pumps were used with either LISPRO formulation described in U.S. Pat. No. 6,034,054 or the regular insulin formulations described in U.S. Pat. No. 4,783,441. While the regular insulin formulations showed the expected 90-day stability, catheter blockages were observed with the LISPRO formulations in only a few weeks. With the LISPRO formulations, the catheters were blocked with material that was identified by mass spectroscopy as a mixture of insulin and Tris in a 10/90 ratio. This surprising finding suggests a potential mechanism of LISPRO precipitation followed by LISPRO-Tris interaction coupled with reaction of $CO_2$ with the Tris to form the di-Tris carbamide.

The invention disclosed herein has a number of embodiments. A preferred embodiment of the invention is a composition which includes a combination of a first insulin species and a second insulin species, wherein the combination of the first and second insulin species is more stable than a composition having only the first insulin species or a composition having only the second insulin species. A related embodiment of the invention is a composition which includes a first insulin species and a second insulin species, wherein the first insulin species and the second insulin species form a heterodimeric complex; and wherein the first insulin species and the second insulin species are selected so that the heterodimeric complex is more stable than a homodimeric complex formed by the first insulin species or a homodimeric complex formed by the second insulin species. As disclosed herein, the relative stability of compositions having the first and second insulin species can be determined by a number of methods known in the art. Preferably the stability of the compositions are determined by a spectrophotometric assay of turbidity or an assay with Thioflavin-T (as illustrated, for example in Example 2).

Typical embodiments of the invention are compositions where the first insulin species is human insulin and the second insulin species is a variant of human insulin having at least one amino acid substitution such as LISPRO insulin. In such embodiments, the human insulin preferably comprises from about 1% to about 50% of the insulin of the composition (and more preferably from about 5% to about 20%) and wherein the LISPRO insulin comprises from about 50% to about 99% of the insulin of the composition (from about 95% to about 80%). As is known in the art, these the compositions can include a variety of factors such as pharmaceutical carriers. Typically the percentages of the insulin species of the composition relate to the relative amounts of insulin units (U) in the composition (see, e.g. the Examples below).

The present invention provides methods of stabilizing insulin molecules in solution as well as stabilized insulin compositions. In particular, as disclosed herein, insulin compositions consisting of a mixture of human insulin and a human insulin analog have a greater stability than compositions consisting of single insulin species. General embodiments of the invention include compositions consisting of a mixture of human insulin and a human insulin analog, wherein the insulin/insulin heterodimer generated by combining human insulin and a human insulin analog is more stable than the insulin homodimers found in solutions of human insulin alone or human insulin analog alone. A typical embodiment of the invention consists of a composition consisting of a mixture of human insulin and a human insulin analog, wherein the human insulin comprises from about 1% to about 50% of the insulin molecules present in the composition and wherein the insulin analog comprises from about 50% to about 99% of the insulin molecules in the composition. Typically the human insulin analog used in such formulations is LISPRO insulin.

Another embodiment of the invention consists of a substantially pure (i.e. is substantially free of non insulin species) insulin heterodimer composition consisting of human insulin and a human insulin analog, wherein the insulin-insulin analog heterodimer is more stable than an insulin/insulin homodimer or the insulin analog/insulin analog homodimer. Yet another embodiment of the invention consists of a process for preparing a stabilized insulin formulation consisting of the steps of combining human insulin with a human insulin analog so that an insulin/insulin analog heterodimer is formed; comparing the stability of the insulin/insulin analog heterodimer with the stability of the insulin/insulin homodimer or the insulin analog/insulin analog homodimer; and selecting a stabilized insulin formulation wherein the insulin/insulin analog heterodimer is more stable than either the insulin/insulin homodimer or the insulin analog/insulin analog homodimer.

In preferred embodiments discussed herein, the stable heterodimers of the invention consist of human insulin and LISPRO insulin. While these insulin species are described as representative species that generate the stable heterodimers of invention, embodiments of the invention encompass stable heterodimers that are formed by combining any two of the wide variety of insulin species that are known in the art in order to generate a stable heterodimer. These insulin species include variants of human insulin such as the LysB28ProB29-human insulin and AspB28 human insulin species discussed herein as well as bovine, porcine and other mammalian insulin species identified in the art as useful in treating pathologies associated with insulin deficiency. Because the present invention provides methods for identifying stable heterodimers, any insulin species capable of forming such stabilized heterodimeric complexes are readily identified by the methods disclosed herein. In a specific embodiment insulin is a monomeric insulin analog selected from the group consisting of LysB28ProB29-human insulin and AspB28 human insulin. In another specific embodiment insulin is bovine or porcine insulin. Consequently, embodiments of the invention include a wide variety of combinations of insulin species that are able to form the stabilized heterodimers of the invention such as human insulin/human insulin analog heterodimers, human insulin analog/human insulin analog heterodimers (wherein different human insulin analogs comprise the heterodimer), human insulin/bovine (or porcine etc.) insulin heterodimers, bovine (or porcine etc.) insulin/human insulin analog heterodimers, bovine insulin/porcine insulin heterodimers, bovine (or porcine etc.) insulin/bovine (or porcine etc.) insulin analog heterodimers etc.

As will be understood in the art, it is possible that not all combinations of insulin species form stabilized heterodimers (as compared to their respective homodimers). Therefore artisans will readily assess the ability of two insulin species to form stable dimers by methods known in the art including those disclosed in the Examples below. By using such methods to assess various insulin formulations, artisans can generate formulations in which the insulin species are specifically selected for desirable properties such as enhanced stability.

The insulin compositions of the invention are preferably in a carrier; preferably a pharmaceutically-acceptable carrier. Suitable carriers and their formulations are described in *Remington's Pharmaceutical Sciences,* 16th ed., 1980, Mack Publishing Co., edited by Oslo et al. Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. It will be apparent to those persons skilled in the art that certain carriers may be more preferable depending upon, for instance, the route of administration and concentration of insulin composition being administered.

The concentration of the insulin species in the present formulations typically ranges from 1.2 mg/ml to 50 mg/ml. A preferred range of insulin concentration is from about 3.0 mg/ml to about 35 mg/ml. More preferred concentrations are about 3.5 mg/ml, about 7 mg/ml, about 14 mg/ml, about 17.5 mg/ml, and about 35 mg/ml which correspond approximately to formulations having about 100 units, about 200 units, about 400 units, about 500 units, and about 1000 units of insulin activity per ml, respectively.

The concentration of zinc in the formulations ranges from about 0.5 µg/ml to about 370 µg/ml, and should be such that at least two zinc atoms are available to complex with the six insulin molecules in each hexamer. The ratio of total zinc (complexed zinc plus uncomplexed zinc) to insulin analog hexamer should be between 2 and 4. A ratio of about 3 to about 4 atoms of total zinc per insulin analog hexamer complex is preferred.

The minimum concentration of phenolic preservative that is required to form the monomeric insulin analog hexamer in the present formulations. For some purposes, such as to meet compendial preservative effectiveness requirements for multi-use formulations, the concentration of phenolic preservative in the present formulations may be increased above that required to form hexamers to an amount necessary to maintain preservative effectiveness. The concentration of preservative necessary for effective preservation depends on the preservative used, the pH of the formulation, and whether substances that bind or sequester the preservative are also present. Generally, the amount necessary can be found in, e.g., WALLHAUSER, K. D H., DEVELOP. BIOL. STANDARD. 24, pp. 9–28 (Basel, S. Krager, 1974). When formulated, the insulin analog hexamer complex used in the present formulation binds as many as seven phenolics, though generally, only six phenolics are bound to the hexamer. A minimum of about three phenolics is required for hexamer formation. When preservative is required for antimicrobial effectiveness, the preferred phenolic concentration is about 23 mM to about 35 mM. M-cresol and phenol, either separately or in mixtures, are preferred preservatives.

The formulations may optionally contain an isotonicity agent. The formulations preferably contain an isotonicity agent, and glycerin is the most preferred isotonicity agent. The concentration of glycerin, when it is used, is in the range known in the art for insulin formulations, preferably about 16 mg/ml.

In addition to utilizing a insulin/insulin analog mixture to provide a stabilized insulin formulation, the utilization of additional stabilizers typically used in the art are also contemplated for use in the formulations described herein. For example, methionine is included in the disclosed pharmaceutical formulations as a means to effectively inhibit the oxidation of methionine residues in the protein. In addition, nonionic surfactants such as polysorbate 80 may be included to inhibit the damage to polypeptides that can occur with freeze-thawing and mechanical shearing. Moreover, EDTA and other known scavengers of metal ions (which are known to catalyze many oxidation reactions), may be added to further stabilize the compositions.

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) may optionally be added to the formulation. These additives are not required to achieve the great advantage of the present invention, but may be useful if the formulations will contact plastic materials.

Administration may be via any route known to be effective by the physician of ordinary skill. Parenteral administration is preferred. Parenteral administration is commonly understood as administration by other than a gastrointestinal route. Preferred parenteral routes for administering the formulations of the present invention include intravenous, intramuscular, subcutaneous, intraperitoneal, intraarterial, nasal, pulmonary, and buccal routes. Intravenous, intraperitoneal, intramuscular, and subcutaneous routes of administration of the compounds used in the present invention are more preferred parenteral routes of administration. Intravenous, intraperitoneal, and subcutaneous routes of administration of the formulations of the present invention yet more highly preferred.

Administration via certain parenteral routes may involve introducing the formulations of the present invention into the body of a patient through a needle or a catheter, propelled by a sterile syringe or some other mechanical device such as an continuous infusion system. A formulation provided by the present invention may be administered using a syringe, injector, pump, or any other device recognized in the art for parenteral administration. A formulation of the present invention may also be administered as an aerosol for absorption in the lung or nasal cavity. The formulations may also be administered for absorption through the mucus membranes, such as in buccal administration.

The amount of a formulation of the present invention that is administered to treat a pathology such as diabetes or hyperglycemia depends on a number of factors, among which are included, without limitation, the patient's sex, weight and age, the underlying causes of the condition or disease to be treated, the route of administration and bioavailability, the persistence of the administered monomeric insulin analog in the body, the formulation, and the potency of the monomeric insulin analog. Where administration is intermittent, the amount per administration should also take into account the interval between doses, and the bioavailability of the monomeric insulin analog from the formulation. Administration of the formulation of the present invention could be continuous. It is within the skill of the ordinary physician to titrate the dose and infusion rate or frequency of administration of the formulation of the present invention to achieve the desired clinical result.

Monomeric insulin analogs used in the present invention can be prepared by any of a variety of recognized peptide synthesis techniques including classical solution methods, solid phase methods, semi-synthetic methods, and recombinant DNA methods. Chance, et al., U.S. Pat. No. 5,514, 646, issued May 7, 1996, discloses the preparation of various monomeric insulin analogs with sufficient detail to enable one skilled in the art to prepare any of the monomeric insulin analogs used in the present invention.

Both zinc and a phenolic preservative are used to achieve a complex that is stable and capable of rapid dissociation and onset of action. The hexamer complex consists of two zinc ions per hexamer of human insulin analog, and at least three molecules of a phenolic preservative selected from the group consisting of chlorocresol, m-cresol, phenol, and mixtures thereof. Soluble monomeric insulin analog is converted to the hexamer complex by dissolving the monomeric insulin analog in a diluent containing the phenolic preservative in suitable quantities at a pH of about 7 to about 8 and then adding zinc. Zinc is preferably added as a zinc salt, such as, without limitation, zinc acetate, zinc bromide, zinc chloride, zinc fluoride, zinc iodide, and zinc sulfate. The skilled artisan will recognize that there are many other zinc salts which also might be used to make the monomeric insulin analog complexes that are part of the present invention. Preferably, zinc acetate, zinc oxide, or zinc chloride is used because these compounds do not add new chemical ions to commercially accepted processes.

Dissolution of the monomeric insulin analog may be aided by what is commonly known as "acid dissolution." For acid dissolution, the pH the aqueous solvent is lowered to about 3.0 to 3.5 with a physiologically tolerated acid, preferably HCl, to aid in the dissolution of the monomeric analog. Other physiologically tolerated acids include, without limitation, acetic acid, citric acid, and sulfuric acid. Phosphoric acid is preferably not used to adjust pH in preparing the formulations of the present invention. The pH is then adjusted with a physiologically tolerated base, preferably sodium hydroxide, to about pH 7.3 to 7.5. Other physiologically tolerated bases include, without limitation, potassium hydroxide and ammonium hydroxide. Thereafter, the phenolic preservative and zinc are added.

Methods of the Invention

Parenteral formulations of the present invention can be prepared using conventional dissolution and mixing procedures. To prepare a typical formulation for example, a measured amount of insulin and insulin analog is combined with the desired preservative, a zinc compound, and the buffering agent, in water in sufficient quantities. The formulation is generally sterile filtered prior to administration. Variations of this process would be recognized by one of ordinary skill in the art. For example, the order the components are added, the order in which pH is adjusted, if any, the temperature and ionic strength at which the formulation is prepared, may be optimized for the concentration and means of administration used.

Yet another embodiment of the invention is a method of making an insulin composition by combining a first insulin species and a second insulin species under conditions that allow the formation of a heterodimeric complex and where the first insulin species and the second insulin species are selected to form a heterodimeric complex that is more stable than a homodimeric complex formed by the first insulin species or a homodimeric complex formed by the second insulin species. A related embodiment of the invention is a method of making an insulin composition by combining a first insulin species and a second insulin species where the resulting composition is more stable than a composition having only the first insulin species or a composition having only the second insulin species. Yet another embodiment of the invention is a method of stabilizing an insulin composition that consists of a first insulin species and a second insulin species by specifically selecting the first and second insulin species in order to generate a composition that is more stable than a composition having only the first insulin species or a composition having only the second insulin species. As disclosed herein, the relative stability of compositions having the first and second insulin species can be determined by a number of methods known in the art. Preferably the stability of the compositions are determined by a spectrophotometric assay of turbidity or an assay with Thioflavin-T (as illustrated, for example in Example 2).

Typical embodiments of the invention are compositions where the first insulin species is human insulin and the second insulin species is a variant of human insulin having at least one amino acid substitution such as LISPRO insulin. In such embodiments, the human insulin preferably comprises from about 1% to about 50% of the insulin of the composition (and more preferably from about 5% to about 20%) and wherein the LISPRO insulin comprises from about 50% to about 99% of the insulin of the composition (from about 95% to about 80%). As is known in the art, these the compositions can include a variety of factors such as pharmaceutical carriers. Typically the percentages of the insulin species of the composition relate to the relative amounts of insulin units in the composition (see, e.g. the Examples below).

Another embodiment of the invention is a method for identifying a stabilized insulin composition which includes the steps of combining a first insulin species with a second insulin species so that a heterodimeric complex formed from the first and second insulin species is generated, comparing the stability of the heterodimeric complex formed from the first and second insulin species with the stability of a homodimeric complex formed from the first insulin species or a homodimeric complex formed from the second insulin species and identifying a formulation wherein the heterodimeric complex formed from the first and second insulin species is more stable than homodimeric complex formed from the first insulin species or a homodimeric complex formed from the second insulin species. A related embodiment of the invention is a method for identifying a stabilized insulin composition which includes the steps of combining a first insulin species with a second insulin species and comparing the stability of the formulation having a combination of the first and second insulin species with the stability of a formulation having only the first insulin species or a formulation having only the second insulin species and identifying an insulin composition wherein the formulation generated by combining the first and second insulin species is more stable than a formulation having only the first insulin species or a formulation having only the second insulin species.

As disclosed herein, the relative stability of compositions having the first and second insulin species can be determined by a number of methods known in the art. Preferably the stability of the compositions are determined by a spectrophotometric assay of turbidity or an assay with Thioflavin-T (as illustrated, for example in Example 2).

Typical embodiments of the invention are compositions where the first insulin species is human insulin and the second insulin species is a variant of human insulin having at least one amino acid substitution such as LISPRO insulin. In such embodiments, the human insulin preferably comprises from about 1% to about 50% of the insulin of the composition (and more preferably from about 5% to about 20%) and wherein the LISPRO insulin comprises from about 50% to about 99% of the insulin of the composition (from about 95% to about 80%). As is known in the art, these the compositions can include a variety of factors such as pharmaceutical carriers. Typically the percentages of the insulin species of the composition relate to the relative amounts of insulin units in the composition (see, e.g. the Examples below).

Another embodiment of the invention consists of a method of stabilizing an insulin polypeptide prone to aggregation by combining the insulin polypeptide with an insulin analog polypeptide in an amount sufficient to form an insulin polypeptide/insulin analog polypeptide heterodimer, wherein the insulin polypeptide/insulin analog polypeptide heterodimer is more stable than either an insulin polypeptide/insulin polypeptide homodimer or an insulin analog polypeptide/insulin analog polypeptide homodimer.

Yet another embodiment of the invention consists of a method of stabilizing an insulin analog prone to aggregation consisting of combining the insulin analog with insulin in an amount sufficient to form an insulin-insulin analog heterodimer, wherein the insulin/insulin analog heterodimer is more stable than an insulin analog/insulin analog homodimer.

Another embodiment of the invention consists of a process for identifying a stabilized multispecies insulin/insulin heterodimer by first combining one insulin species (e.g. human insulin) with a second insulin species (e.g. a human insulin analog) so that a multispecies insulin/insulin heterodimer is formed. In these methods, the stability of the multispecies insulin/insulin heterodimer is compared with the stability of the homodimers formed by each insulin species. In this manner one can identify a stabilized multispecies insulin/insulin heterodimers by determining whether the multispecies heterodimer is more stable than either of the homodimers formed by each insulin species. Another embodiment of the invention includes a stabilized multispecies insulin/insulin heterodimer identified by this process.

There are a number of procedures known in the art to be useful in evaluating the stability of insulin compositions. Such methods include spectrophotometric measurements of dynamic light scatttering, gel permeation chromatography, near- and far-ultraviolet circular dichroism etc. (see, e.g. Baudys et al., J Pharm Sci 1995 January;84(1): 28–33; Bugamelli et al., Arch Pharm (Weinheim) 1998 April; 331 (4): 133–138; and Bremas et al., Biochemistry 1990 2;29 (39): 9289–9293).

Additional methods for determining insulin stability are provided in the Examples below. Briefly, these methods include two phases. The first phase includes the following steps. Preparing a statistically relevant number of identical samples of a protein formulation to yield a one or more sample types, where the protein is susceptible to changes in its native conformation yielding non-native conformers of the protein. A small molecular agent or probe that yields a change upon binding to a non-native conformer of the protein is then added to the samples. Preferably the probe is Thioflavin-T. A controlled stress is then applied to all sample types, where the controlled stress applied causes the protein to exhibit a change in its native conformation. The sample types are then monitored to yield time-dependent data that are related to a degree of protein conformational change for each sample type. The second phase includes applying a survival analysis to the data obtained for each sample type and comparing the survival analysis for each sample type to determine the relative physical stability of the protein formulations under evaluation. A preferred controlled stress suitable for use in embodiments of the invention is agitation. A preferred method to monitor the change in protein conformation is via fluorescence. An example of a protein conformational change suitable for use in the invention is the change in the physical structure of insulin from its native conformation to the fibril form of insulin.

Other embodiments of the invention consists of methods for treating diabetes consisting of administering an effective dose of the above-mentioned formulations to a patient in need thereof A related embodiment of the invention consists of a method for treating hyperglycemia consisting of administering an effective dose of the disclosed formulation a patient in need thereof. In a preferred embodiments of these methods, the formulation is administered using a continuous infusion system.

The present invention is further detailed in the following Examples which are offered by way of illustration and are not intended to limit the invention in any manner. All patent and literature references cited in the present specification are hereby incorporated by reference in their entirety.

EXAMPLES

Example 1

Stability of Insulin Heterodimers

In a laboratory experiment a formulation of mixed LISPRO/Human insulin in a ratio of 90/10 showed better physical stability to physical insult than an equivalent formulation of recombinant human insulin and better pH stability than LISPRO alone. We have investigated several possible formulations and find that the preferred formulation comprises between 80 and 90 percent LISPRO with the balance being human insulin, derived from either semi-synthetic or recombinant technology. See Example 3 below.

Example 2

Assessing Stability of Insulin Compositions

As is known in the art, there ate a wide variety of methods that can be used to evaluate the stability of insulin compositions including spectrophotometric measurements of dynamic light scatttering, gel permeation chromatography, near- and far-ultraviolet circular dichroism etc. (see, e.g. Baudys et al., J Pharm Sci 1995 January;84(1): 28–33; Bugamelli et al., Arch Pharm (Weinhein) 1998 April; 331 (4): 133–138; and Bremas et al., Biochemistry 1990 2;29 (39): 9289–9293).

As disclosed herein, the conformational status (which is known to be related to a proteins stability) of insulin can also be evaluated with a spectroscopic agent or probe that preferentially binds to a non-native conformer of insulin (e.g. one exhibiting a non-native β-pleated sheet conformation). One example of a small molecular spectroscopic probe of protein structure is Thioflavin-T. Protocols are provide below as illustrative examples of methods that can be used to asses the physical stability of insulin compositions.

Typical embodiments of such methods involve placing a small amount of an insulin formulation to be evaluated under a controlled stress. This controlled stress is physically translated to the protein contained in a particular formulation. A comparison of two or more protein formulations that differ in composition then yields the relative physical stability of the proteins formulations under evaluation. In such assays, a typical sample volume is about 50 $\mu$l to about 500 $\mu$l, most preferably about 200 $\mu$l. The medium chosen for the analysis can be any medium in which the physical stability of a particular protein is desired to be evaluated, such as aqueous solutions, organic solvents, and the like.

A change in the physical state of a protein such as insulin, i.e., production of one or more non-native protein states, is detected spectroscopically using an spectroscopic probe that preferentially binds to a non-native form of the protein, as compared to its binding to the native form of the protein. The detection of this induced change in protein state, caused by the applied stress, can be observed by following a concomitant change in spectra of the spectroscopic probe upon its binding to a non-native state of the protein. This change in the spectra of the spectroscopic probe can be monitored by numerous spectral techniques, such as fluorescence, absorbance, nuclear magnetic resonance (NMR), circular dichroism (CD), or the like.

Other embodiments of the invention include monitoring a change in the physical state of protein by observing changes in the bulk physical properties of the protein formulations under evaluation. These techniques involve monitoring a change in shape and/or size of the protein as a function of the applied stress, including monitoring changes in the frictional properties, viscosity, turbidity, light scattering, or the like, of the protein formulations under evaluation. The use of these techniques in embodiments of the invention do not require the addition of a spectroscopic agent to probe the change in the conformational state of the protein in a given formulation.

The stress applied is preferably a controlled physical stress, including agitational, vibrational, rotational, shearing, ultrasonic stresses, or the like. Other types of applied stress are included in embodiments of the invention, such as thermal stress, photochemical stress, or the like. When applying a thermal stress, concomitant changes in the physical states of the protein result, however, thermal stress also may affect the chemical state of the protein. In embodiments of the invention utilizing a photochemical stress, generally changes in the photochemical state of the protein is probed. Further, the controlled stress applied can be a combination of two or more stresses, such as agitation of the protein formulations of interest at elevated temperatures.

As noted above, the spectroscopic agent or probe is preferably a small molecule that preferentially binds to a non-native conformer of the protein. One example of a small molecular spectroscopic probe of protein structure is Thioflavin-T. Thioflavin-T is a fluorescent dye that has been widely used for the detection of amyloid fibrils. In the presence of fibrils, and perhaps other protein configurations as well, Thioflavin-T gives rise to a new excitation maximum at about 450 nm and enhanced emission at about 482 nm when bound to a fibril protein form. Unbound Thioflavin-T is essentially non-fluorescent at these wavelengths. Recently, Thioflavin-T has been used to elucidate the mechanism of fibril formation in insulin (see, e.g. Nielson, et al., *Biochemistry*, 2001, 40, p. 6036). Other small molecules can be used as probes of the changes in protein structure from native to non-native states. Examples of other small molecular, spectroscopic probes is the "exposed hydrophobic patch" probe and the "exposed coordination site" probe. A "hydrophobic patch" probe preferentially binds to exposed hydrophobic patches of a protein. These hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline, or the like. Other spectroscopic probes are metal-amino acid complexes, such as cobalt metal complexes of hydrophobic amino acids, such as phenylalanine, leucine, isoleucine, methionine, and valine, or the like. As is the case with Thioflavin-T, these small molecular, spectroscopic probes yield a spectroscopic change upon binding to a non-native form of the protein of interest, such as a change in fluorescence, a change in absorbance, a change in circular dichroism, and the like.

Another example of a small molecular probe, is a probe of the coordination saturation in non-native states of a metalloprotein. Examples of these molecular probes are spectroscopically active and unsaturated coordination metal complexes, such as ruthenium-pyridyl complexes, ruthenium-phenanthroline complexes, or the like. These spectroscopic probes bind to one or mote exposed coordination sites in non-native conformations of a metalloprotein. These exposed coordination sites generally are bound to specific amino acid ligands in the native protein, but become open to coordination by the small molecular probe in non-native states of the metalloprotein.

Other spectroscopic systems utilizing spectroscopic probes also can be utilized in embodiments of the invention, such as fluorescence systems based on FRET (fluorescence resonance energy transfer) and PET (photo-induced electron transfer), such as those disclosed in U.S. Pat. No. 6,011,984, and the like, which is incorporated by reference in its entirety herein.

After gathering spectroscopic data reflective of the physical stability of one or more protein formulations, these data are compared using survival curve analyses. These survival curve analyses are statistical methods similar to those that have been used in the prior art, for example, in the analysis of data from clinical trials of a new pharmaceutical drug. In these clinical trials the survival of patients taking the drug is compared to the survival of patients taking a placebo or another drug. Thus, at the end of the trial, a percent survival is obtained for each patient population. As with any statistical method, the number of individuals, or samples, i.e., an N value, should be chosen to yield statistically significant results. In an embodiment of the invention that utilizes a 96 well microplate, as described below, the N value chosen is preferably about 16 to about 48 identical sample formulations with an N value of about 24 identical samples being most preferred. Other N values also may be used depending of the size of the microplate utilized, or other similar device for containing the samples.

In preferred embodiments of the invention, the survival curve analysis compares the rate of protein aggregation of a first sample type, containing a statistically relevant number of identical samples of a particular insulin formulation, to that of one or more samples types containing a statistically relevant number of identical samples of different insulin formulations. In particular embodiments of the invention, protein aggregation, or changes in protein conformation, is equated with non-survival of the protein.

A protein reference batch of known physical stability can be used to estimate the physical stability of particular unknown insulin formulations. A comparison to a reference protein batch controls for small changes in starting conditions that can affect the absolute rate of aggregation, as well as controlling drift in the light source intensity and detector sensitivity. These small changes and drifts can affect the absolute intensity measurements Additionally, the possibility of dye bleaching by incident radiation can be addressed by using a protein reference batch. Thus, the use of a protein reference batch controls for random variables in the experimental protocol. However, a protein reference batch is not necessary to the evaluation of the relative physical stability of a series of protein formulations. In this experimental design, each protein formulation acts as a reference to the other protein formulations under evaluation. Thus, the relative physical stability of a series of protein formulations can be determined without the use of a protein reference batch.

In a preferred assay, the median survival time for particular protein samples to reach a state where 50% of the protein is in an aggregated state, or 50% of the protein has not survived, is chosen as an end point of the experimental run. This end point is preferred as a metric and appears to adequately represent the physical stability of a given protein formulation. In other embodiments of the invention, other points on the survival curve can be used as a metric of the physical stability of the protein formulations under evaluation. The median survival, however, appears to represent and coincide with the average physical stability of the sample formulations. Thus in embodiments of the invention, the longer the median survival, the greater is the physical stability of the protein formulations under evaluation.

A survival curve analysis of the change in physical state of a particular protein is highly preferable because direct evaluation of the physical stability of protein formulations is difficult, to nearly impossible, to obtain simply from a profile of protein aggregation versus time. There are two main reasons for this difficulty. The first reason is experimental. The raw data are very noisy mostly due to a stirring device, such as Teflon bead, being in the light path of the fluorometer, as described below. The second reason is that the kinetics of aggregation is not well understood. For insulin, it has been proposed that the process of aggregation is autocatalytic (see, e.g. Sluzky et al., *Proceedings of the National Academy of Sciences,* 1991, 88 p. 9377). The actual reaction mechanism of aggregation of insulin, which includes fibril formation, however, is largely unknown. Accordingly an analytical solution to the aggregation kinetic mechanism of insulin is also unknown.

The use of a survival curve analysis applied to the spectroscopic data of changes in protein states yields a simple method which compares a statistically relevant number of samples of a given formulation to a statistically relevant number of samples of another formulation, yielding a relative physical stability profile of the sample types under evaluation. Accordingly, no prior knowledge or understanding of the mechanism of aggregation, or the mechanism of protein conformational changes, is needed for applications of embodiments of the invention.

Once aggregation profiles are obtained for each sample type under evaluation, a calculation of the time to reach a certain fluorescence level is performed. This time to reach a certain fluorescence level is generally set at 50% survival, but can vary with the needs of particular experiments. This end point of the survival analysis represents a point in the aggregation profile that is at least beyond the initiation of aggregation. Moreover, the level of fluorescence obtained at the 50% survival point was determined to yield reliable results. This level of fluorescence is generally substantially greater than the background noise of the system and ensures that the results are statistically relevant. For experimental systems with greater or less noise, higher or lower levels of fluorescence can be set as end points.

The data typically consists of a series of times to the initiation of aggregation. Once the time to start aggregation is calculated, a standard Kaplan-Meier survival curve analysis (see, e.g. Campbell, M., and Machin, D., *Medical Statistics,* Wiley, New York, 1983. p. 112), where survival fractions are calculated as a function of time, is applied. For a comparison between the formulations of interest and a reference batch, for example, the log rank test equivalent to the Mantel-Haenszel test is performed. This test generates a P value testing the null hypothesis that the survival curves are identical.

Other important information that can be obtained from comparing two survival curves is their median survival and the ratio of the median survival of a reference batch, or other protein sample type, to the median survival of the sample type of interest. Median survival, as described above, is the time for 50% of the samples to reach a pre-determined level of fluorescence. If the samples do not show fluorescence at the end of the experiment, then median survival cannot be computed and we can only estimate a "minimum" median survival.

In the following typical protocol, the physical stability of particular insulin formulations are evaluated using a preferred embodiment of the accelerated physical stability method of the invention. However, the accelerated physical stability methods of the embodiments of the invention can be used to evaluate any protein that undergoes a change in conformation due to an application of a controlled stress.

A first step is to physically stress the insulin formulations under evaluation by controlled agitation. A series of identical insulin samples are prepared to yield a first sample type, or reference batch in this example, and another series of identical insulin samples are prepared to yield a second sample type. A small volume of each insulin sample is placed in an open well, i.e., exposed to air, of a 96-well microplate. One or more small, stirring device(s), preferably in the form of Teflon (polytetrafluoroethylene) bead(s), is also placed in each sample well. The Teflon bead has a very hydrophobic surface, which increases the interfacial tension within each well. However, the stirring device can be made of different materials, including hydrophilic materials Thioflavin-T, which is shown to bind to aggregated protein states is then added to each sample well (see, e.g. Levine, H., *Protein Science,* 1993, 2, p. 404).

Although this particular embodiment of the invention exposes the protein formulations to air, and thus increasing the interfacial tension, i.e., exposure to a air-water interfaces, other embodiments of the invention utilize placing the protein samples in sealed vials from which residual air is evacuated, thereby reducing the air-water interface. The physical stress applied is agitation of the microplate in a commercial instrument that also measures the fluorescence of Thioflavin-T as a function of the time of agitation. A typical instrument suitable for use in the accelerated physical stability methods of the invention is a Fluorskan fluorescence plate reader (Lab-systems). In this embodiment, the plate is orbitally agitated. However other forms of agitation, such as shaking and vibrating, are suitable for use in other embodiments of the invention. After a certain time of agitation, a curve is generated, which is a plot of aggregation, as measured by the increase in Thioflavin-T fluorescence intensity, as a function of time. The data generated are then subjected to a survival curve analysis.

A typical experiment begins by adding approximately 200 microliters of a given insulin formulation (e.g. a combination of insulin species to be examined) into multiple wells in the 96-well microplate. A single Teflon bead is added to the well together with an aliquot of Thioflavin-T dissolved in water. The microplate is covered with a Mylar sheet to reduce evaporation and avoid against accidental particulate contamination. The covered microplate is then placed in an incubated orbital shaker and is agitated with a controlled force. The preferred operational parameters are given in the Table 1.

TABLE 1

Operational Parameters for Protein Stability Estimation

Sample volume: 150–250 μl preferably 190 μl
Thioflavin-T: 10–30 μM, preferably 20 μM
Shaking speed: 480–1200 rpm, preferably 960 rpm
Shaking diameter: 1–5 mm, preferably 1 mm
Temperature: 25–40° C., preferably 37° C.
Microplate cover: 1–3 sheets of Mylar covers preferably one sheet.
Excitation wavelength: 440 nm–500 nm, preferably about 444 nm
Emission wavelength: 480 nm–520 nm, preferably about 510 nm
Measurement directions: top down
Number of wells per formulation: $\geq 24$
Run time: 3–9 days or until more than 50% of the samples start to aggregate A representative snap shot of an aggregation profile for a single run using all 96 wells can then be taken. This snap shot gives the observer a quick look at the experimental results without any further analysis. A snap shot is taken at every measurement during the entire run. Once an aggregation profile is obtained, the time to reach a certain fluorescence level (e.g. 50) is calculated, which in this example represents the definite initiation of aggregation. The particular fluorescence level can be determined from a comparison to the background noise to ensure that the fluorescence level chosen is above the background noise. Once the time to start aggregation is calculated (e.g. $t_{50}$) one can plot a survival curve, where survival fractions are calculated using Kaplan-Meier method. These calculations ate performed using commercially available software, such as Prism or an equivalent software.

Example 3
In Vivo Efficacy of Insulin Heterodimers

In a preliminary in-vivo demonstration, a formulation of U1000 comprising 850 U/ml of LISPRO and 150 U/ml of recombinant human insulin effectively controlled diabetes in a canine model for several months with no difficulties.

What is claimed is:

1. A method of making an insulin heterodimer composition, the method comprising:
   (a) selecting a first insulin species comprising human insulin and a second insulin species comprising a human insulin polypeptide having an amino acid substitution at position 28 in the beta chain;
   (b) adding the first insulin species and the second insulin species together in a aqueous solution comprising a pharmaceutically acceptable carrier;
   (c) allowing the first insulin species and the second insulin species to associate in the solution so that the insulin heterodimer composition is made;
   wherein the first insulin species and the second insulin species are selected so that the heterodimer formed by the first insulin species and the second insulin species is more stable than a homodimer formed by the second insulin species.

2. The method of claim 1, wherein the second insulin species is AspB28 insulin.

3. The method of claim 1, wherein the second insulin species is LISPRO insulin.

4. The method of claim 3, wherein the human insulin comprises from about 1% to about 50of the insulin of the composition and wherein the LISPRO insulin comprises from about 50% to about 99% of the insulin of the composition.

5. The method of claim 4, wherein the human insulin comprises from about 5% to about 20% of the insulin of the composition and wherein the LISPRO insulin comprises from about 95to about 80% of the insulin of the composition.

6. The method of claim 1, wherein the composition is a pharmaceutical composition.

7. A method of stabilizing an insulin composition comprising:
   (a) selecting a first insulin species comprising human insulin and a second insulin species comprising:
      a human insulin polypeptide having a P28D amino acid Substitution in the insulin beta chain; or
      a human insulin polypeptide having a P28K/K29P amino acid substitution in the insulin beta chain;
   wherein the first insulin species and the second insulin species are selected such that a heterodimer formed by the first insulin species and the second insulin species is more stable than a homodimer formed by the second insulin species;
   (b) adding the first insulin species and the second insulin species together in a aqueous solution comprising a pharmaceutically acceptable carrier;
   (c) allowing the first insulin species and the second insulin species to associate in the solution so that a insulin heterodimer is formed by the first insulin species and the second insulin species;
   so that the insulin composition is stabilized.

8. The method of claim 7, wherein the second insulin species is AspB28 insulin.

9. The method of claim 7, wherein the second insulin species is LISPRO insulin.

10. The method of claim 9, wherein the human insulin comprises from about 1% to about 50% of the insulin of the composition and wherein the LISPRO insulin comprises from about 50% to about 99% of the insulin of the composition.

11. The method of claim 10, wherein the human insulin comprises from about 5% to about 20% of the insulin of the composition and wherein the LISPRO insulin comprises from about 95% to about 80% of the insulin of the composition.

12. The method of claim 11, wherein the composition is a pharmaceutical composition.

13. A method of making an insulin heterodimer composition, the method comprising:
   (a) adding human insulin and LISPRO insulin together in an aqueous solution comprising a pharmaceutically acceptable carrier;
   (b) allowing the human insulin and LISPRO insulin to associate in the solution so that the insulin heterodimer composition is made;
   wherein the human insulin and LISPRO insulin are selected so that a heterodimer formed by the human insulin and LISPRO insulin is more stable than a homodimer formed by the human insulin or a homodimer formed by the LISPRO insulin.

14. The method of making an insulin heterodimer composition, the method comprising:
   (a) selecting a first insulin species comprising human insulin and a second insulin species comprising a variant of human insulin polypeptide having at least one amino acid substitution;
   (b) adding the first insulin species and the second insulin species together in a aqueous solution comprising a pharmaceutically acceptable carrier;
   (c) allowing the first insulin species and the second insulin species to associate in the solution so that the insulin heterodimer composition is made;
   wherein the first insulin species and the second insulin species are selected so that the heterodimer formed by the first insulin species and the second insulin species is more stable than a homodimer formed by the second insulin species.

* * * * *

UNITED STATES PATENT AND TRADEMARK OFFICE
CERTIFICATE OF CORRECTION

PATENT NO. : 6,852,694 B2
DATED : February 8, 2005
INVENTOR(S) : William Peter Van Antwerp et al.

It is certified that error appears in the above-identified patent and that said Letters Patent is hereby corrected as shown below:

Column 23,
Line 39, "50of" should read -- 50% of --.
Line 46, "95to" should read -- 95% to --.
Line 55, "Substitution" should read -- subsititution --.

Signed and Sealed this

Sixteenth Day of August, 2005

JON W. DUDAS
*Director of the United States Patent and Trademark Office*